(12) United States Patent
Jassemidis et al.

(10) Patent No.: US 8,197,395 B2
(45) Date of Patent: Jun. 12, 2012

(54) PACEMAKER FOR TREATING PHYSIOLOGICAL SYSTEM DYSFUNCTION

(75) Inventors: Leonidas D. Jassemidis, Scottsdale, AZ (US); Konstantinos S. Tsakalis, Chandler, AZ (US)

(73) Assignee: Arizona Board of Regents for and on Behalf of Arizona State University, Scottsdale, AZ (US)

( * ) Notice: Subject to any disclaimer, the term of this patent is extended or adjusted under 35 U.S.C. 154(b) by 968 days.

(21) Appl. No.: 11/632,456

(22) PCT Filed: Jul. 14, 2005

(86) PCT No.: PCT/US2005/024864
§ 371 (c)(1),
(2), (4) Date: Aug. 18, 2008

(87) PCT Pub. No.: WO2006/019822
PCT Pub. Date: Feb. 23, 2006

(65) Prior Publication Data
US 2009/0264952 A1 Oct. 22, 2009

Related U.S. Application Data

(60) Provisional application No. 60/587,513, filed on Jul. 14, 2004.

(51) Int. Cl.
*A61M 21/00* (2006.01)
*A61B 5/04* (2006.01)
(52) U.S. Cl. ......................................... 600/26; 600/544
(58) Field of Classification Search .................. 607/45; 600/26, 544, 545
See application file for complete search history.

(56) References Cited

U.S. PATENT DOCUMENTS

| 4,201,224 | A  | * | 5/1980  | John ............................... 600/544 |
| 6,304,775 | B1 |   | 10/2001 | Iasemidis et al. ............. 600/544 |
| 6,488,617 | B1 | * | 12/2002 | Katz ................................ 600/26 |
| 6,671,555 | B2 |   | 12/2003 | Gielen et al. ..................... 607/45 |
| 2003/0105409 | A1 | * | 6/2003 | Donoghue et al. ............. 600/545 |
| 2003/0171689 | A1 | * | 9/2003 | Millan et al. ................... 600/544 |
| 2005/0021104 | A1 |   | 1/2005 | DiLorenzo ....................... 607/45 |
| 2005/0240242 | A1 | * | 10/2005 | DiLorenzo ....................... 607/45 |

OTHER PUBLICATIONS

Grassi and Tsakalis, "PID Controller Tuning by Frequency Loop-Shaping: Application to Diffusion Furnace Temperature Control," *IEEE Trans. Contr. Systems Technology*, 8:842-847, 2000.
Grassi et al., "Adaptive/Self-Tuning PID Control by Frequency Loop-Shaping," *Proc. IEEE 39$^{th}$ Conf. Decision and Control*, 2:1099-1101, 2000.

(Continued)

*Primary Examiner* — Carl H. Layno
*Assistant Examiner* — Jon-Eric C. Morales
(74) *Attorney, Agent, or Firm* — Fulbright & Jaworski L.L.P.

(57) ABSTRACT

Disclosed is a device and method for preventing seizures due to physiological system dysfunction. The method is based on a conjectural model of the brain wherein each brain site is modeled as a chaotic oscillator; a normal brain generates an internal feedback signal to prevent long-term entrainment among the oscillators; and a pathological brain fails to provide this feedback signal. The device of the present invention measures and characterizes the brain sites to determine if entrainment is occurring among the oscillators, derives an appropriate feedback signal to counteract the entrainment, and applies the feedback signal to the critical brain sites. The feedback signal generated by the device supplements or takes the place of the feedback signal that would otherwise be generated by the normal brain.

26 Claims, 7 Drawing Sheets

OTHER PUBLICATIONS

Grassi et al., "Integrated Identification and PID Controller Tuning by Frequency Loop-Shaping," *IEEE Trans. Contr. Systems Technology*, 9:285-294, 2001.

Iasemidis et al., "On the prediction of seizures, hysteresis and resetting of the epileptic brain: insights from models of coupled chaotic oscillators," *Order and Chaos*, 8:283-305, 2003.

Tsakalis and Iasemidis, "Control aspects of a theoretical model for epileptic seizures," *Int. J. Bifurcation and Chaos*, 16(7):2013-2027, 2006.

Tsakalis et al., "A feedback control systems view of epileptic seizures," *Cybernetics and Systems Analysis*, 42:483-495, 2006.

* cited by examiner

PACEMAKER FOR TREATING PHYSIOLOGICAL SYSTEM DYSFUNCTION

This application claims the benefit of U.S. Provisional Patent Application No. 60/587,513, filed on Jul. 14, 2004, which is hereby incorporated by reference for all purposes as if fully set forth herein.

BACKGROUND OF THE INVENTION

1. Field of the Invention

The present invention relates primarily to physiological nonlinear dynamical system control. More particularly, the present invention involves a system and method to predict and prevent seizures caused by neurological dysfunction.

2. Discussion of the Related Art

Epilepsy is a chronic disorder characterized by recurrent brain dysfunction caused by paroxysmal electrical discharges in the cerebral cortex. If untreated, an individual afflicted with epilepsy is likely to experience repeated seizures, which typically involve some level of impaired consciousness. Some forms of epilepsy can be successfully treated through medical therapy. However, medical therapy is less effective with other forms of epilepsy, including Temporal Lobe Epilepsy (TLE) and Frontal Lobe Epilepsy (FLE). With TLE and FLE, removing the portion of the hippocampus and/or cerebral cortex responsible for initiating the paroxysmal electrical discharges, known as the epileptogenic focus, is sometimes performed in an effort to control the seizures.

Although this discussion substantially focuses on epileptic seizure, it will be apparent to one of ordinary skill that the discussion may also apply to any other dynamical disorders of the brain, such as Parkinson's Disease, migraines and schizophrenia, as well as of other physiological systems that involve internal pathological (malfunctioning) control.

Related art approaches to seizures generally involve either detection of a seizure in its early phases, or prediction of seizure onset. Detection approaches generally measure neural activity using electroencephelography (EEG) and identify spikes in EEG data (or some other anomaly) that are consistent with the onset of seizure. Prediction is more sophisticated, whereby certain sites of the brain are measured and characterized, either structurally or functionally, and the measurements or characterizations are correlated with known conditions that signal impending seizure.

For prediction, functional measurement and characterization of brain sites generally identify changes in neural activity at certain brain sites, and predict the onset of seizure by correlating specific measured neural behavior with known indicators of seizure onset. Structural measurement and characterization of brain sites include identifying changes in the impedance of brain tissue between electrodes. Changes in impedance between particular brain sites may be correlated with the onset of seizure in certain patients. Other approaches include comparing signal propagation delay times between different brain sites.

Structural and functional approaches to prediction of seizure onset may involve either passive or active measurements, or a combination of both. Active structural measurements generally involve applying a known signal stimulus and measuring the signal after propagating through a portion of the brain to determine parameters such as impedance. Active functional measurements generally involve applying a known stimulus signal and measuring a change in neural behavior of a given brain site in response to the applied signal.

Certain related art functional approaches to prediction include measuring and characterizing the chaoticity of certain brain sites, and identifying entrainment between a pair of brain sites. As disclosed in U.S. Pat. No. 6,304,775 to Iasemidis et al., identifying entrainment between brain sites can provide notice of seizure susceptibility hours, if not days, before seizure onset.

For detection, EEG data is generally processed to identify the early stages of a seizure through traditional signal processing algorithms, such as frequency domain, wavelet, and neural network implementations. The results of such processing are compared with predetermined thresholds to identify seizure onset.

Although related art methods have demonstrated the ability to predict the onset of seizure, an equally sophisticated method for effective control is lacking. For example, many related art prediction systems, having predicted the onset of a seizure, generally attempt to mitigate the seizure by methods such as releasing anti-seizure medication into the patient's bloodstream, applying high amplitude electrical shocks to the relevant brain sites, or applying sensory stimuli (such as visual) to the patient, all of which are traditional treatment methods.

Certain related art approaches to control seizures involve the use of stimulation based on prediction of onset, so that the stimulation may be more effective in preventing epileptic seizure. In other words, the earlier the prediction, the more effective the prevention. U.S. Pat. No. 6,671,555 to Gielen et al, uses an active measurement technique to measure functional connectivity of the brain; correlates a decrease in functional connectivity with seizure onset; and applies high frequency pulses to prevent the seizure before it occurs. Apparent drawbacks of this approach are as follows: the estimation of the connectivity measure requires high levels of signal injection, especially since the estimation must be done quickly; and the correcting signal (pulses) is generic and coarse. Accordingly, excessive stimulation power is generally required, and there may be cases where such stimulation is ineffective. Published U.S. Patent Application, Publication No. 2005/0021104 by DiLorenzo mentions the use of control laws to apply feedback stimuli to brain sites based on detected neural activity, but does not address how to use feedback to take advantage of the chaotic nature of neural activity, or how to use control with prediction in order to prevent a seizure before it starts.

Other related art approaches to seizure mitigation involve open loop application of signals in a preprogrammed manner. Examples of open loop approaches include continuously stimulating the vagus nerve or the thalamus with predetermined stimulation signals. Generally, open loop approaches do not involve any sensing and predicting of seizures and only stimulate the brain to prevent seizure. As such, they are expected to be less effective and less efficient than closed-loop approaches.

In all of the cases described, seizure mitigation or control is generally primitive compared to the state of related art approaches to prediction. In other words, although considerable insight has been gained into neural structure and function related to predicting seizures, mitigation and control approaches do not take advantage of this insight and instead rely on more traditional treatments.

SUMMARY OF THE INVENTION

Accordingly, the present invention is directed to a pacemaker for treating physiological system dysfunction that substantially obviates of the aforementioned problems due to limitations and disadvantages of the related art. In general, the present invention achieves this by providing a device and method for predicting the onset of an epileptic seizure by continuously evaluating the chaoticity of various locations of the brain, adaptively identifying control parameters sufficient to reestablish chaoticity, identifying converging entrainment in the brain, and applying control signals to disentrain the centers of the brain that are beginning to entrain for abnormally long time intervals.

An advantage of the present invention is that it prevents the onset of a seizure with minimal electrical stimulation.

Another advantage of the present invention is that it more effectively prevents seizures by supplementing natural feedback mechanisms that otherwise prevent entrainment.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, a method for treating a dynamical disorder is provided, which comprises acquiring a plurality of signals corresponding to a plurality of electrodes, wherein the plurality of electrodes corresponds to a plurality of brain sites; computing a correlation between a number of signals within the plurality of signals, the number of signals corresponding to a number of brain sites within the plurality of brain sites; computing a feedback signal that is a function of the correlation and the number of signals; and applying the feedback signal to a number of transmit electrodes within the plurality of electrodes, the number of transmit electrodes corresponding to the number of brain sites.

In another aspect of the present invention, the aforementioned and other advantages are achieved by a device for treating a dynamical disorder, which comprises a plurality of electrodes corresponding to a plurality of brain sites; and a microprocessor having a computer readable medium encoded with a program for acquiring a plurality of signals corresponding to the plurality of electrodes; computing a correlation between a number of signals within the plurality of signals, the number of signals corresponding to a number of brain sites within the plurality of brain sites; computing a feedback signal that is a function of the correlation and the number of signals; and applying the feedback signal to a number of transmit electrodes within the plurality of electrodes, the number of transmit electrodes corresponding to the number of brain sites.

In another aspect of the present invention, the aforementioned and other advantages are achieved by a method for treating a dynamical disorder, which comprises acquiring a plurality of signals corresponding to a plurality of electrodes, the plurality of electrodes corresponding to a plurality of brain sites identifying entrainment between a number of brain sites within the plurality of brain sites; and performing neurocontrol on the number of brain sites, based on a result of identifying entrainment.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE ILLUSTRATED EMBODIMENTS

The invention operates according to a paradigm whereby the brain includes a network of chaotic oscillators. Each chaotic oscillator represents a different brain site. Under normal circumstances, the chaotic oscillators operate in a state of spatiotemporal chaos such that there is substantially no correlation in behavior between any two oscillators. The "chaoticity" of the brain may be measured and characterized such that the loss of spatiotemporal chaos can be observed, and any increase in correlation, or coupling, between two brain sites (hereinafter "critical sites") can be identified as creating the conditions under which seizure is imminent.

The loss of spatiotemporal chaos between oscillators at critical sites may be seen as resulting from pathological (improperly tuned) feedback between the oscillators at the critical sites. An epileptic seizure is one possible manifestation of pathological feedback whose byproduct is also a loss of spatiotemporal chaos. The loss of spatiotemporal chaos may be due to, or related to, anomalies internal to the brain, such as a deficiency in certain electrolytes, neurotransmitters, neuroreceptors, abnormal network functional and/or structural connections etc. in the relevant brain sites.

The oscillators at different brain sites may be represented as a network of N Rossler oscillators (hereinafter "oscillators") that are subject to diffusive coupling. The use of Rossler oscillators for representing brain sites is described in the paper by Iasemidis, L. D., Prasad, A., Sackellares, J. C., Pardalos, P. M. and Shiau, D. S., [2003] "On the prediction of seizures, hysteresis and resetting of the epileptic brain: insights from models of coupled chaotic oscillators," in *Order and Chaos*, Bountis, T. and Pneumatikos, S., Eds. vol. 8, Publishing House of K. Sfakianakis, Thessaloniki: Greece, pp. 283-305 (Proc. of the 14th Summer School on Nonlinear Dynamics: Chaos and Complexity, Patras, Greece, 2001), which is hereby incorporated by reference as if fully set forth herein.

Each $i^{th}$ of the N oscillators may be represented as follows:

$$\frac{\partial x_i}{\partial t} = -\omega_i y_i - z_i + b_i + \sum_{j=1, j \neq i}^{N} (\varepsilon_{i,j} x_j - \varepsilon'_{i,j} x_i) + u_{i,j}$$

$$\frac{\partial y_i}{\partial t} = \omega_i x_i + \alpha_i y_i$$

$$\frac{\partial z_i}{\partial t} = \beta_i x_i + z_i (x_i - \gamma_i)$$

where $x_i$, $y_i$, and $z_i$ are system variables, or internal states, of the $i^{th}$ oscillator; and $\alpha$, $\beta$, $\gamma$, $\omega$ are intrinsic parameters that are chosen in the chaotic regime. For example, for the purpose of modeling, these parameters may have values of approximately 0.4, 0.33, 5, and 0.95, respectively. For our purposes, $x_i$ may be considered as mimicking a time sequence EEG signal. The parameter $b_i$ is a constant bias term, one per oscillator, which may be chosen at random between a specified range, such as [−0.2, 0.2]. The $u_{ij}$ term refers to an internal feedback signal between the $i^{th}$ and the $j^{th}$ oscillators, which is described below. According to the present invention, the internal feedback signal $u_{ij}$ is assumed to be applied through neural interconnections between the brain sites corresponding to the $i^{th}$ and the $j^{th}$ electrodes.

The $\epsilon_{i,j}$ and $\epsilon'_{i,j}$ terms are asymmetric coupling factors between the $i^{th}$ and the $j^{th}$ oscillators. The coupling factor $\epsilon_{i,j}$ may be represented as a general coupling function of $x_j$ and $x_i$, namely, $\epsilon_{i,j}\{x_j,x_i\}$. Under symmetric coupling, the two asymmetric coupling factors $\epsilon_{i,j}$ and $\epsilon'_{i,j}$ have substantially equal weights $\epsilon_{i,j}$, and the coupling function may take a special form $\epsilon_{i,j}\{x_j,x_i\}=\epsilon_{i,j}(x_j-x_i)$.

If the value of the coupling factor $\epsilon_{i,j}$ increases, the spatiotemporal chaos between the $i^{th}$ and the $j^{th}$ oscillators diminishes, and Short Term Lyapunov exponent corresponding to oscillator i ($STL_{max,i}$) and oscillator j, ($STL_{max,j}$) converge. The corresponding diffusive coupling between the two oscillators is referred to as entrainment. Conversely, disentrainment refers to the reduction of diffusive coupling between the oscillators. In a particular example, the Lyapunov exponents begin to converge for values of $\epsilon_{i,j}$ greater than about 0.1, and spatiotemporal chaos may be considered lost for values of $\epsilon_{i,j}$ greater than about 0.25. Note that any correlation between $STL_{max,i}$ and $STL_{max,j}$ may be coincidental. It is not the near equality in Lyapunov exponent value that corresponds to entrainment; it is the convergence of Lyapunov exponent values that marks the onset of entrainment. As such, the mutual trajectories of the respective Lyapunov exponents, and not their values at any given time, mark the loss of spatiotemporal chaos and the beginning of entrainment.

Figure 1:
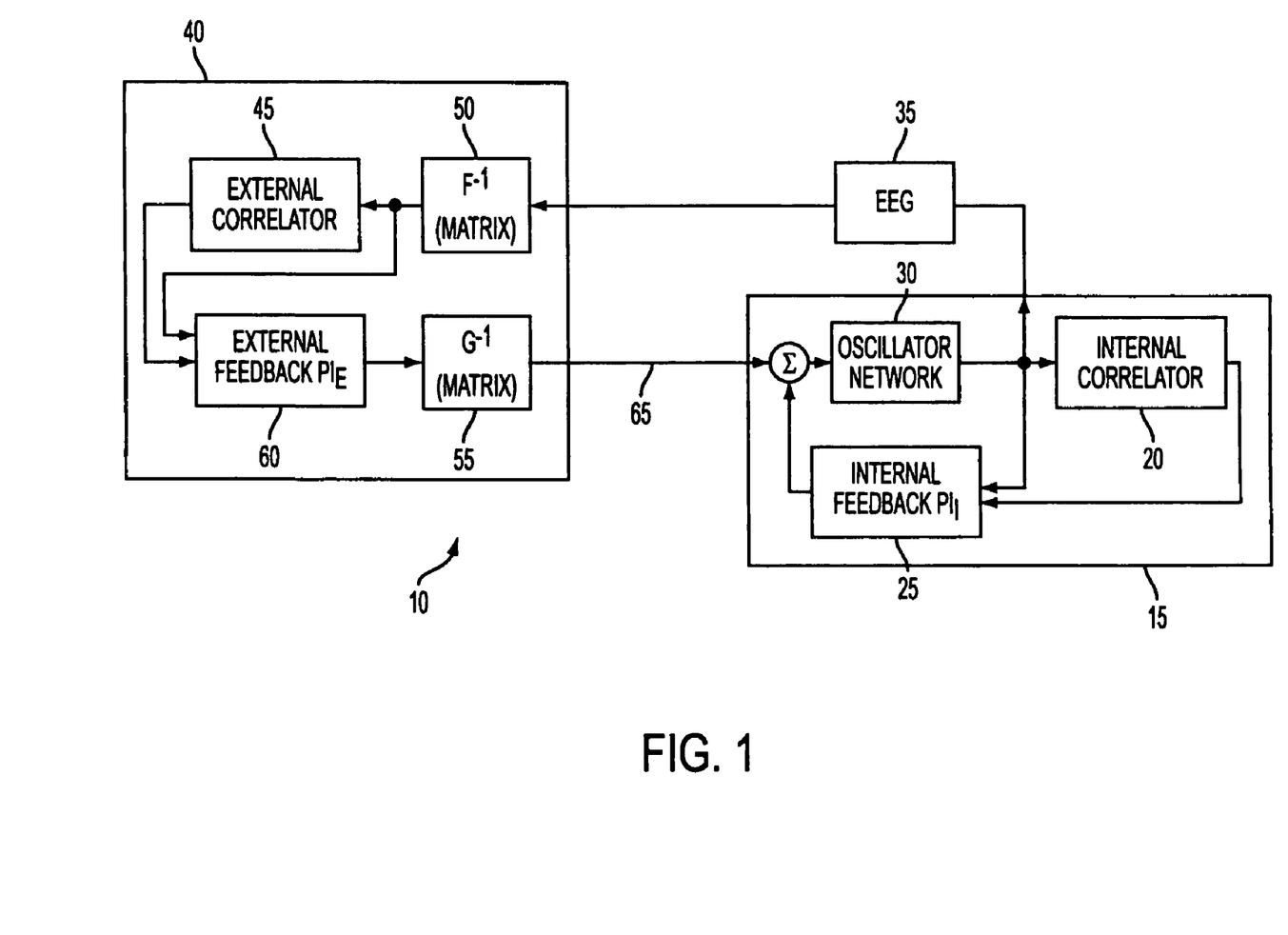
FIG. 1 illustrates a control architecture and a conjectural functional depiction of the brain.

Under normal brain function, the internal feedback signal $u_{ij}$ substantially negates entrainment between the $i^{th}$ and the $j^{th}$ oscillators, thereby disentraining the corresponding brain sites. For this purpose, $u_{ij}$ may be defined as follows:

$$u_{i,j}=-k_{i,j}\{x_j,x_i\},$$

where the function $k_{i,j}\{x_j,x_i\}$ approximates the coupling factor function $\epsilon_{i,j}\{x_j,x_i\}$ described above. For example, in one case of symmetric coupling $k_{i,j}\{x_j,x_i\}=k_{i,j}(x_j-x_i)$, and $k_{i,j}$ is a multiplication factor (gain). In this case, the value of gain factor $k_{i,j}$ may be recursively updated by the internal feedback controller 25 of a normal brain to approximate the coupling factor $\epsilon_{i,j}$. An exemplary approach to recursively updating the gain factor $k_{i,j}$ is through an update law such as the following relation:

$$k_{i,j}=PI\{corr[x_i,x_j]-c^*\}$$

where PI refers to a Proportional Integral feedback mechanism, or controller, which is known to the art of control systems; "corr" denotes the correlation between the signals $x_i$ and $x_j$; and $c^*$ is a threshold parameter. For purposes herein, a threshold value of about 0.1 may be selected for $c^*$. PI feedback mechanisms are discussed further in K. J. Astrom and Hagglund, *PID controllers: Theory, Design, and Tuning*, 2nd edn. ISA, Research Triangle Park, NC, U.S.A., 1995; E. Grassi, K. Tsakalis, S. Dash, S. V. Gaikwad, W. MacArthur and G. Stein, "Integrated Identification and PID Controller Tuning by Frequency Loop-Shaping," *IEEE Trans. Contr. Systems Technology*, 9, 2, 285-294, March 2001; E. Grassi and K. Tsakalis, "PID Controller Tuning by Frequency Loop-Shaping: Application to Diffusion Furnace Temperature Control," *IEEE Trans. Contr. Systems Technology*, 8, 5, 842-847, September 2000; and E. Grassi, K. Tsakalis, S. Dash, S. Gaikwad, G. Stein, "Adaptive/Self-Tuning PID Control by Frequency Loop-Shaping," *Proc. IEEE 39th Conf. Decision and Control*, V.2, 1099-1101, Sydney, Dec. 12-15, 2000, which are incorporated by reference as if fully set forth herein. The control parameters for the PID controllers may be understood as referring to the proportional gain, the integral gain, and the differential gain, and that the control parameters for adaptive controllers are variables that may be treated as states. It will be readily understood by one of ordinary skill that the control parameters will depend on the type of controller used.

In addition to a PI feedback controller, other feedback mechanisms, such as Proportional Integral Differential (PID) controllers, may be used. Examples of other linear, nonlinear, and adaptive mechanisms, which are also applicable here, are described in the following texts: D. G. Luenberger, *Linear and Nonlinear Programming, 2nd Edition*. Addison Wesley, Reading, Mass., 1984; D. P. Bertsekas, *Nonlinear Programming*. Athena Scientific, Belmont, Mass., 1995; G. C. Goodwin and K. S. Sin, *Adaptive Filtering Prediction and Control*. Prentice Hall, Englewood Cliffs, N.J., 1984; and P. A. Ioannou and J. Sun, *Robust Adaptive Control*. Prentice Hall, NJ, 1996, which are hereby incorporated by reference as if fully set forth herein. The common characteristic of all such schemes is their objective to reduce the correlation or entrainment between brain sites.

Finally, the correlation term "corr" between signals is used to signify a general measure of synchronization or entrainment between signals. Examples of correlation include but are not limited to the T-index of $STL_{max}$, correlation coefficients over running windows, and exponentially weighted correlation coefficients. Correlation may be based on other types of entrainment, such as phase lock or frequency correlation.

According to the control paradigm of the present invention, the applied stimulus, or external feedback signal, is an external PI-based feedback between the $i^{th}$ and the $j^{th}$ oscillators that emulates the internal feedback in the brain. Its role is to supplement the internal feedback signal and cancel the effect of excessive diffusive coupling between two oscillators at corresponding brain sites, and thereby maintain the correlation $corr[x_i,x_j]$ below a threshold $c^*$. The external feedback signal denoted by $u_{i,j}^E$ is activated to negate any excessive and persistent entrainment between the $i^{th}$ and the $j^{th}$ oscillators, thereby disentraining the corresponding brain sites. For this purpose, and similarly to the internal feedback, $u_{i,j}^E$ may be defined as follows:

$$u_{i,j}^E=-k_{i,j}^E\{x_j,x_i\}$$

where the function $k_{i,j}^E\{x_j,x_i\}$ approximates the coupling factor function $\epsilon_{i,j}\{x_j,x_i\}$, less the internal coupling. For the case of symmetric coupling $k_{i,j}^E\{x_j,x_i\}=k_{i,j}^E(x_j-x_i)$ and $k_{i,j}^E$ is a multiplication factor (gain). As before, the value of gain factor $k_{i,j}^E$ may be updated recursively to approximate the effective coupling factor. An exemplary approach to recursively updating the gain factor $k_{i,j}^E$ is through an update law such as the following relation:

$$k_{i,j}^E=PI\{corr[x_i,x_j]-c^*\}$$

where PI refers to a Proportional Integral feedback mechanism; "corr" denotes a general measure of correlation between the signals $x_i$ and $x_j$; and $c^*$ is a threshold parameter.

The threshold may be an adjustable parameter, tuned adaptively or based on preliminary tests run during the device set-up. The PI-based external feedback signal $u_{i,j}^E$ maintains the chaotic behavior of the oscillator network (described below) in the presence of variations in the coupling factor $\epsilon_{i,j}$ and despite the pathological internal feedback control. As previously discussed in the analysis of the internal feedback paradigm, other feedback, adaptive, or optimization techniques can be used to define the mechanism for updating the gain factor $k_{i,j}^E$, or the function $k_{i,j}^E\{x_j,x_i\}$ in the general case. In all cases, the objective of the external feedback mechanism is to reduce the coupling in the conjectural coupling structure of the brain, and to decouple the various brain sites.

The application of the external feedback signal $u_{i,j}^E$ is a form of neurocontrol. In particular, it is a form of neuromodulation whereby the applied external feedback signal $u_{i,j}^E$ is summed with the internal feedback signal $u_{ij}$ to disentrain the critical sites.

FIG. 1 illustrates an exemplary control architecture 10 according to an embodiment of the present invention. Control architecture 10 includes a controller segment 40 and a brain segment 15. The brain segment 15 includes paradigmatic components of the brain that the controller segment 40 senses and stimulates to prevent a seizure.

Brain segment 15, which is a conjectured functional description of the brain, includes an oscillator network 30; an internal correlator 20; and an internal feedback PI controller 25. The oscillator network 30 is a plurality of N oscillators described above. The internal correlator 20 is a hypothetical mechanism that determines the correlation or synchronization corr$[x_i,x_j]$ between each pair of $i^{th}$ and $j^{th}$ oscillators. The internal feedback controller 25 derives an internal feedback signal $u_{ij}$ corresponding to each pair of $i^{th}$ and $j^{th}$ oscillators, based on the correlation output by the internal correlator 20. The internal feedback signal $u_{ij}$ derived by the internal feedback controller 25 is fed to the oscillator network 30 (summed with any external feedback signal $u_{i,j}^E$ generated by the controller segment 40, which is described below). Although the discussion focuses on pairs of brain sites, it applies to other numbers and combination of brain sites as well. Accordingly, all mention of pairs of electrodes and brain sites may refer to any number of brain sites showing entrainment.

According to the control paradigm of the present invention, the internal feedback controller 25 derives and applies an internal feedback signal $u_{ij}$ for each pair of $i^{th}$ and $j^{th}$ oscillators to maintain spatiotemporal chaos between each pair of oscillators. In a pathological brain, the internal feedback controller 25 fails to derive or apply an adequate internal feedback signal $u_{ij}$ to maintain spatiotemporal chaos, providing the conditions in which entrainment may occur.

According to the present invention, controller segment 40 computes and applies an external feedback signal $u_{i,j}^E$ 65, which it applies to the oscillator network 30 of the brain segment 10 in order to supplement the inadequate internal feedback signal $u_{ij}$ derived and applied by the internal feedback controller 25.

The controller segment 40 includes an $F^{-1}$ filter 50, which is an inverse matrix of a filter F described below; an external correlator 45; an external feedback PI controller 60; and a $G^{-1}$ filter 55, which is an inverse matrix of a filter G described below.

According to the exemplary control architecture, filter F is a collection of dynamical systems, linear or nonlinear, which describe the relationship between the output signal of a brain site with the corresponding measured output signal. In other words, F is the relation, or filter, between the signal at a brain site and the signal as measured by an EEG. For example, if $x_i$ refers to the output of a brain site (such as a critical site), and $x'_i$ refers to the corresponding nearby measurement, then the two are related by $x'_i=F_i[x_i]$. An example of F may be a simple first order filter having a transfer function $$F_i(s) = \frac{b_1 s + b_0}{s + a_1}.$$

This exemplary form of F can be sufficient to adjust the phase of the measured signal to match the signal at the brain site. In other words, the simple first order filter above may sufficiently define the relation between the signal present at a brain site and the same signal as measured by the EEG. Other forms of F are possible, such as nonlinear filters, similar to the one above but with coefficients that depend on other measured outputs or states, e.g., whether the patient is awake or asleep. The most general form of F can be a multivariable function (i.e., with more than one measurement as inputs). However, more general forms of filter F may increase in complexity, which may limit the usefulness of such a general form where large data sets are available. In other words, a more specific (and thus more computationally efficient) form of F may be heuristically derived as more EEG data is collected and characterized. It will be readily apparent to one of ordinary skill how a more specific form of F may be determined through system identification methods given a set of collected EEG data.

Similarly, filter G represents a collection of dynamical systems, linear or nonlinear, that relate the applied external feedback signal $u_i^E$ (stimulus) to the effective stimulus $u_i^{CS}$ at the critical site. In other words, filter G is the relation between the external feedback signal $u_i^E$ applied to the electrode and the feedback signal $u_i^{CS}$ that impinges on the brain site. The notation $u_i^E$ is used for the total applied external stimulus to a given electrode, which, as explained below, is an integration or summation of the individual computed external feedback signals $u_{i,j}^E$ between pairs of sites.

By identifying and inverting both F and G, the effects of these filters may be compensated so that their effects are removed from the coupling factor $\epsilon_{i,j}$. In general, filters F and G may be minimized by placing transmit and sensor electrodes as close as possible to the brain site so that they most directly measure and effect the signal at the given brain site. In doing so, filters F and G may be assumed to be near identity. As such, $F^{-1}$ filter 50, which is the inverse of the filter F, and a $G^{-1}$ filter 55, which is the inverse of the filter G, are well defined and well behaved.

The respective filter sub-components $F_i$ and $G_i$ of filters F and G may be derived by a preliminary system identification procedure or test, which may be performed once during the initial implant of the device, periodically, or continuously. It will be readily apparent to one of ordinary skill that system identification procedures, such as those implemented in existing software tools, are available and within the scope of the invention. System identification methods are described in L. Ljung, *System Identification: Theory for the user*. Prentice-Hall, NJ, 1987; and G. C. Goodwin and K. S. Sin, *Adaptive Filtering Prediction and Control*. Prentice Hall, Englewood Cliffs, N.J., 1984, which are incorporated by reference as if set forth fully herein.

The correlator 45 acquires the EEG signals that have been transformed by $F^{-1}$ filter 50, and computes a correlation between each pair of EEG signals, which is the corr$[x_i,x_j]$ term in the equation for the gain factor $k_{i,j}$ described above. Correlation may correspond to a set of T-indices relating to STL$_{max}$ values, correlation coefficients over running windows, and exponentially weighted correlation coefficients. As mentioned earlier, correlation may be based on other types of entrainment, such as phase lock or frequency correlation. It will be readily apparent to one of ordinary skill that various methods for computing the correlation between filtered EEG signals are possible and within the scope of the invention.

The external feedback PI controller 60 takes the correlation corr[$x_i, x_j$] computed by correlator 45 and generates a plurality of external feedback signals $u_{i,j}^E$ 65, which includes a signal corresponding to each of the $i^{th}$ and $j^{th}$ oscillators in the oscillator network 30. For the case of diffusive coupling, these signals may take the form $$u_{i,j}^E = G_i^{-1}[-k_{i,j}(F_j^{-1}[x_j] - F_i^{-1}[x_i])]$$

$$u_{j,i}^E = G_j^{-1}[-k_{j,i}(F_i^{-1}[x_i] - F_j^{-1}[x_j])]$$

where, $k_{i,j}$ and $k_{j,i}$ are pure gains (multiplication constants), which are updated using the PI mechanism described above; $F_i$ and $F_j$ are low order nonlinear filters (described above) corresponding to electrical signals $x_i$ and $x_j$ sensed by the EEG 35 at brain sites i and j; and $G_i$ and $G_j$ are low order nonlinear filters (described above), which are the respective transformations of the stimuli applied to brain sites; and $k_{i,j}$ is a function selected and/or updated to approximate the coupling between the brain sites i and j.

Given the external feedback signal $u_{i,j}^E$ for a given pair of oscillators, the external feedback signal that is applied to a single $i^{th}$ oscillator may be the sum of the external feedback signals for all possible $j^{th}$ oscillators. All such contributions are added up to form the external feedback signal $u_i^E$ (stimulus) applied to brain site i:

$$u_i^E = \sum_{i \neq j}^{N} u_{i,j}^E.$$

Alternatively, the summation may only be over the oscillators that show signs of entrainment, which may be a subset of N. Alternatively, the summation may be a weighted summation or a simultaneous integration over time and electrode space. In general, these inputs are combined depending on the form of the coupling, e.g., to accommodate terms that depend on n-tuples of signals instead of pairs.

When the coupling is asymmetric or, more generally, non-diffusive, $k_{i,j}\{x_j, x_i\}$ can be a general function of its variables. In such a case, the expression for the external feedback signal $u_{i,j}^E$ may take the general form $$u_{i,j}^E = G_i^{-1}[-k_{i,j}\{F_j^{-1}[x_j], F_i^{-1}[x_i]\}]$$

$$u_{j,i}^E = G_j^{-1}[-k_{j,i}\{F_i^{-1}[x_i], F_j^{-1}[x_j]\}]$$

The same principles apply, although the complexity of the associated algorithm increases, and the efficiency of the implementation of the algorithm diminishes.

Figure 2:
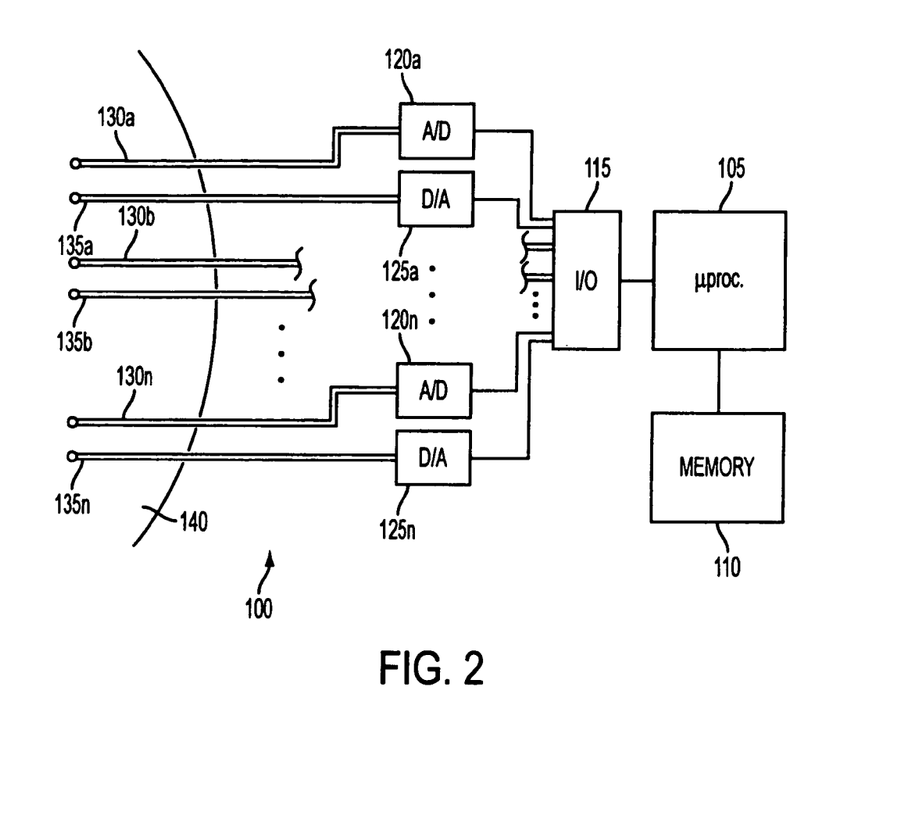
FIG. 2 illustrates an exemplary brain pacemaker device according to the present invention.

FIG. 2 illustrates an exemplary pacemaker device 100 according to the present invention. The pacemaker device includes a microprocessor 105 having a memory 110 and an input/output (I/O) port 115; a plurality of analog to digital (A/D) converters 120a-120n; a plurality of digital to analog (D/A) converters 125a-125n; a plurality of sensor electrodes 130a-130n; and a plurality of transmit electrodes 135a-135b. The pacemaker device further includes a power source (not shown).

The pacemaker device 100 may be implanted within, or disposed externally to the patient. The sensor electrodes 130a-130n and the transmit electrodes 135a-135n may be intracranial and implanted within the patient's brain 140 at predetermined locations. In another embodiment, a pair of sensor and transmit electrodes may co-exist on the same electrode. Alternatively, the electrodes may be noninvasive and located on the patient's scalp. In a particular embodiment of the present invention, the sensor electrodes 130a-130n are intracranial EEG electrodes, and the transmit electrodes 135a-135n are intracranial and located in close proximity to corresponding sensor electrodes 130a-130n. Accordingly, the electrodes are formed as pairs, whereby each transmit electrode 135a-135n is located in close proximity to its corresponding sensor electrode 130a-130n. The purpose for this is to enable each sensor electrode 130a-130n to detect a signal transmitted by its corresponding transmit electrode 130a-135a with minimal cross-coupling, and to maximize the dynamic range of the sensed signal while minimizing the amplitude of the signal transmitted by each of the transmit electrodes 135a-135n.

The microprocessor 105, the memory 110, the I/O port 115, the A/D converters 120a-120n, and the D/A converters 125a-125n may be all or partly be integrated onto the same device. The microprocessor 105 may use an embedded real time operating system, which is stored in memory 110. The microprocessor 105 may include an interface port (not shown) through which it may be connected to a host computer, either through a cable or through a wireless connection. It will be readily apparent to one of ordinary skill that many variations of the microprocessor 105, as well as other components within pacemaker device 100, are possible and within the scope of the present invention.

The memory 110 is encoded with software for implementing the processes according to the present invention, and may have additional memory space for storing configuration parameters and temporary variables. The memory may be all or partly integrated with the microprocessor 105, or may have distributed memory components that communicate with the microprocessor 105 over a wireless connection via the interface port (not shown).

The A/D converters 120a-120d and the D/A converters 125a-125d may each have amplification and signal conditioning stages, and may be individually configured by the microprocessor 105 to have distinct amplifier gains. It will be readily apparent to one of ordinary skill that many variations of amplifiers and signal conditioners are possible and within the scope of the present invention.

Linking FIG. 2 with FIG. 1, the sensor electrodes 130a-130n may be part of the EEG system 35, and each electrode may be located at an oscillator in the oscillator network 30. The transmit electrodes 135a-135n may each be co-located with the respective sensor electrode 130a-130n in the oscillator network 30. The controller segment 40 may be implemented in the software stored in memory 110 and executed on the microprocessor 105. The $F^{-1}$ filter 50, the external correlator 45, the external feedback PI controller 60, and the $G^{-1}$ filter 55 may each be implemented as separate software modules in the software. It will be readily apparent to one of ordinary skill that various software implementations of the controller segment 40 are possible and within the scope of the invention.

Figure 3:
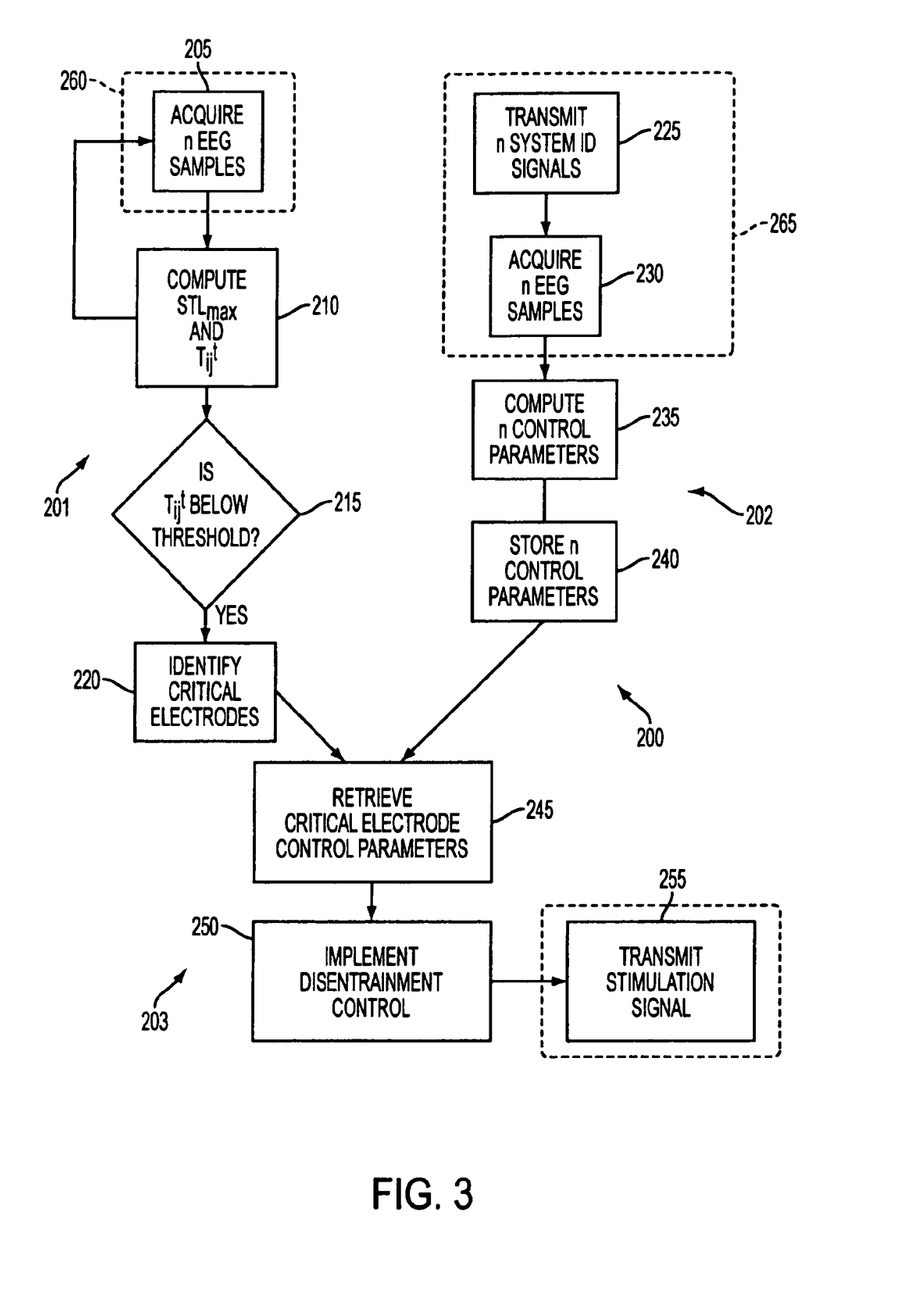
FIG. 3 illustrates an exemplary process for identifying and mitigating entrainment to prevent seizures according to the present invention.

FIG. 3 illustrates an exemplary process 200 for predicting and preventing seizures according to an embodiment of the present invention. Process 200 includes three subprocesses: a prediction subprocess 201, which includes steps 205-220; a system identification subprocess 202, which includes steps 225-240; and a control subprocess 203, which includes steps 245-255. The prediction subprocess 201 and the system identification subprocess 202 may run concurrently and independently, except for the coordination of their respective uses of the A/D converters 120a-120n and D/A converters 125a-125n.

The prediction subprocess 201 encompasses steps 205-220. In step 205, the software acquires EEG samples from each of the n sensor electrodes 130a-130n. Step 205 may run continuously, whereby samples are collected from each sensor electrode 130a-130n at a predetermined sampling period τ. The software acquires the digital data values corresponding to each sample from the respective A/D converters 120a-120n via the I/O port 115, and buffers them in memory 110.

In step 210, the software computes Short Term Lyapunov exponents $STL_{max,i}$ corresponding to each $i^{th}$ of the N sensor electrodes. The software then uses the $STL_{max,i}$ values to compute a set of T-indices, $T_{i,j}^t$, wherein each T-index corresponds to a given pair (i,j) of sensor electrodes. The Short Term Lyapunov exponents $STL_{max,i}$ and T-indices, $T_{i,j}^t$ are explained below.

As illustrated in FIG. 2, the software continuously iterates steps 205 and 210, whereby the software acquires and buffers the acquired EEG samples from each of the N sensor electrodes 130a-130n, and computes and buffers $STL_{max,i}$ values and T-indices $T_{i,j}^t$.

Figure 4:
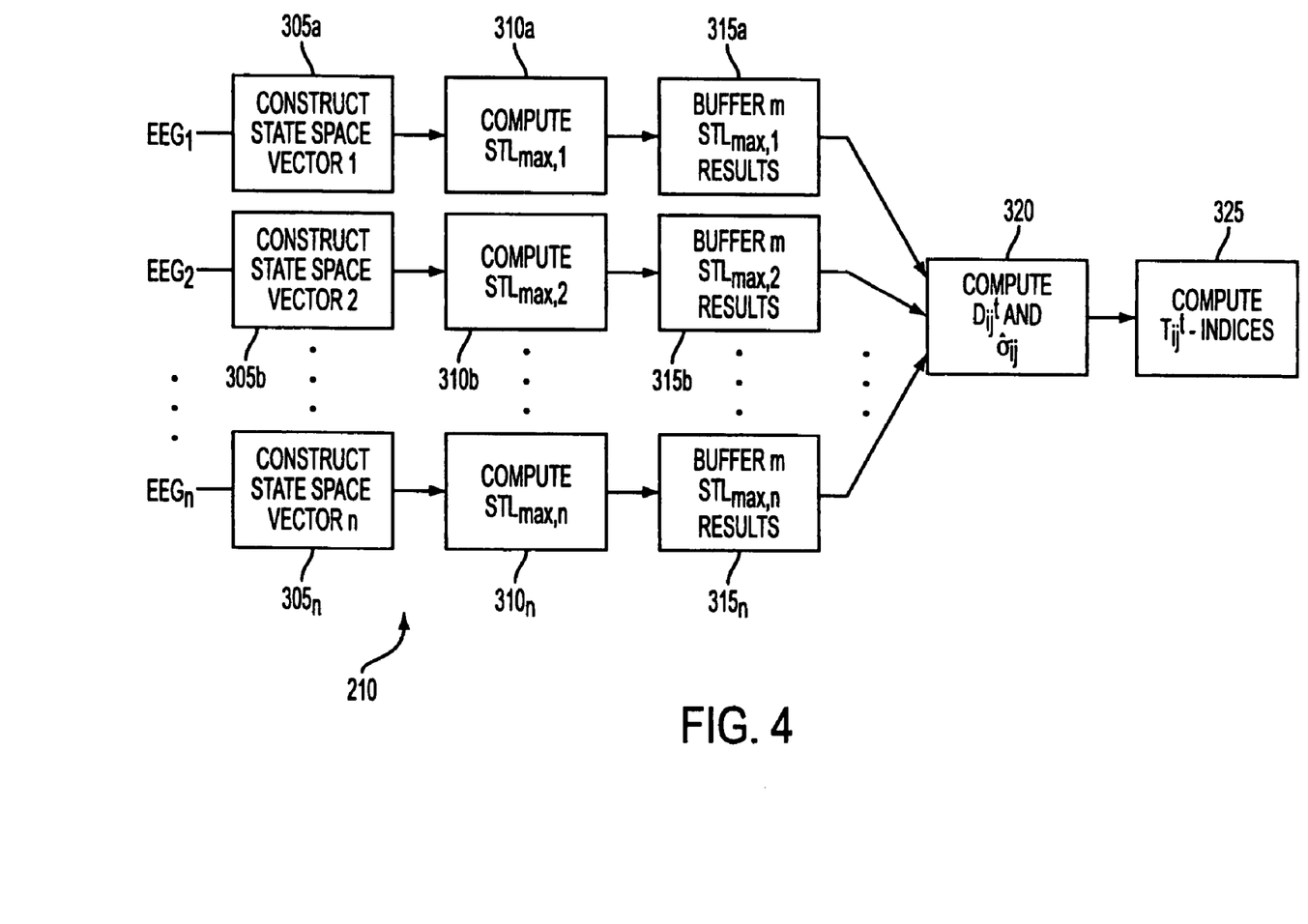
FIG. 4 illustrates an exemplary process for computing Short Term Lyapunov exponents ($STL_{max}$) and T-indices according to the present invention.

FIG. 4 illustrates an exemplary process for computing the Short Term Lyapunov exponents $STL_{max,i}$ and T-indices, $T_{i,j}^t$ in step 215. In steps 305a-305n, N state space vectors are assembled, one per sensor electrode, according to the following relation:

$$x_i(t) = [u_i(t), u_i(t-\tau), \ldots, u_i(t-(d-1)\cdot\tau]$$

where τ is the sampling period; and d is the embedding dimension of the reconstructed state, or the number of EEG samples used to assemble the state space vector; and i is an index referring to a given sensor electrode of the N electrodes.

In steps 310a-310n, a Short Term Lyapunov exponent $STL_{max,i}$ is computed for each i sensing electrode, using the state space vectors assembled in steps 305a-305n. The $STL_{max,i}$ is computed according to the relation $$STL_{max,i} = \frac{1}{N_\alpha} \sum_\alpha L_{i,j}$$

where $N_\alpha$ is the total number of local Lyapunov exponents, which may be equal to the dimension d of the state vector. Each local Lyapunov exponent, $L_{ij}$ may be computed as follows:

$$L_{i,j} = \frac{1}{\Delta t} \cdot \log_2 \left[ \frac{|X(t_i + \Delta t) - X(t_j + \Delta t)|}{|X(t_i) - X(t_j)|} \right]$$

where $X(t_i)$ and $X(t_j)$ are adjacent points (vectors) in the state space, and Δt is the evolution time allowed for the vector difference $|X(t_i) - X(t_j)|$ to evolve to a new difference $|X(t_i + \Delta t) - X(t_j + \Delta t)|$. For example, if Δt is given in seconds (e.g., 60 msec), then $STL_{max,i}$ is given in bits/sec.

In steps 315a-315n, m results of steps 310a-310n are buffered in a sliding window arrangement. Accordingly, for each of the N sensor electrodes, m consecutive values of $STL_{max}$ are stored.

In steps 320-325, a T-index is computed for each pair of sensor electrodes. In step 320, mean $\overline{D}_{i,j}^t$ and standard deviation $\hat{\sigma}_{i,j}^t$ are computed for all m differences $(STL_{max,i} - STL_{max,j})$ within the sliding window buffer assembled in steps 315a-315n. In step 325, T-indices are computed using the results of step 320 as follows:

$$T_{i,j}^t = \frac{|\overline{D}_{i,j}^t|}{\frac{\hat{\sigma}_{i,j}^t}{\sqrt{m}}}.$$

Accordingly, step 325 yields one T-index $T_{i,j}^t$ per unique pair of $i_{th}$ and $j_{th}$ electrodes.

In step 215 of process 200 of FIG. 3, each T-index $T_{i,j}^t$ is compared with a predetermined threshold to determine if any electrode pairs i and j, which correspond to particular sites in the brain, have respective $STL_{max,i}$ values that are converging.

Figure 5A:
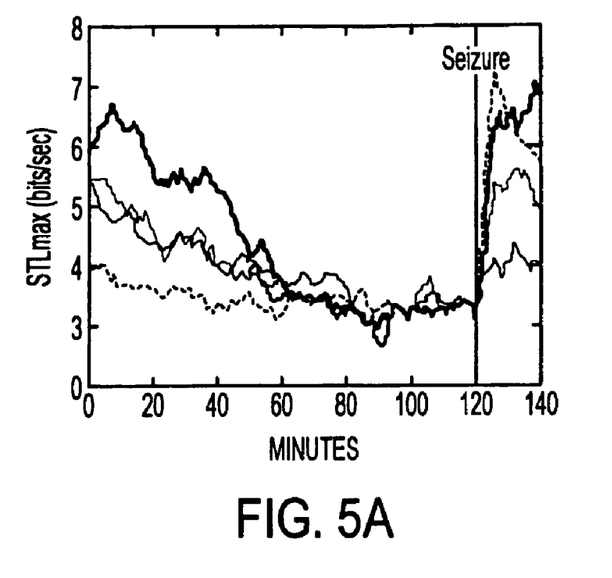
FIGS. 5A and 5B respectively illustrate converging $STL_{max}$ values, and a corresponding T-index, according to the present invention.
Figure 5B:
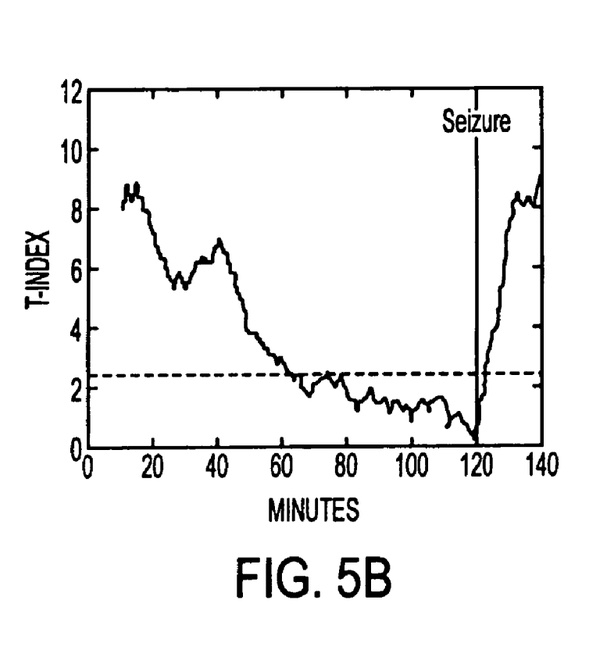

FIGS. 5A and 5B illustrate exemplary data illustrating the relevance the T-index threshold, in which no control is implemented. FIG. 5A illustrates computed $STL_{max}$ values for a plurality of electrodes, which correspond to brain centers undergoing entrainment. The $STL_{max}$ values converge while the brain is in a preictal state before the onset of seizure. FIG. 5B illustrates an average T-index plot corresponding to the $STL_{max}$ data plotted in FIG. 5A. As illustrated in FIG. 5B, once a T-index $T_{i,j}^t$ crosses below a certain threshold, there may be a given amount of time before the onset of seizure. In this example, the T-index threshold is set to about 2.662.

The T-index threshold used in step 215 may be a configuration parameter stored in memory 110. The T-index threshold may be refined by the software, whereby the software stores $STL_{max}$ values and resulting T-indices $T_{i,j}^t$ in memory 110 and estimates an optimal T-index threshold based on past neural activity, as measured by the sensor electrodes 130a-130n.

Steps 225-240, which make up the system identification subprocess 202, may run concurrently with the prediction subprocess 201, described above. In steps 225 and 230, the software issues data values to the D/A converters 125a-125n via the I/O port 115, wherein the data values correspond to a test signal, which are then converted into analog voltages and transmitted by the transmit electrodes 135a-135n. The test signals may be special purpose signals designed for the purpose of most effectively estimating the nonlinear filters $F_i$ and $G_i$ and the parameters for the PI controller, or the test signal may be the external feedback signal $u_{i,j}^E$ that is nominally transmitted to reestablish spatiotemporal chaos between brain sites.

The system identification subprocess 202 of steps 225-240 may run continuously, or may run periodically, depending on the extent to which the brain sites are exhibiting stationary behavior. Accordingly, the software may determine that if the successive executions of the system identification subprocess 202 yield substantially similar nonlinear filters $F_i$ and $G_i$ and PI controller parameters, the software may reduce the frequency at which the system identification subprocess 202 is executed.

In step 230, the software acquires N signals from the sensor electrodes 130a-130n via the A/D converters 120a-120n and the I/O port 115. Steps 225 and 230 are coordinated so that the test signal transmitted by the transmit electrodes 135a-135n are received by sensor electrodes 130a-130n. In step 230, the software stores the data values corresponding to the test signals received by the sensor electrodes 130a-130n in memory 110, along with data values corresponding to the test signal.

In step 235, the software computes the control parameters by deriving PI or PID parameters based on the stored test signal data values and the received signal data values stored in step 230. In the exemplary embodiment of the present invention, the software estimates nonlinear filters $F_i$ and $G_i$ and PI parameters using system identification algorithms like those that are available from commercial control software vendors.

In step 240, the software stores the data values corresponding to estimated nonlinear filters $F_i$ and $G_i$ and gain factors $k_{i,j}$.

Returning to step 220, if any of the T-indices $T_{i,j}{}^t$ cross below the T-index threshold, the software identifies the corresponding $i^{th}$ and $j^{th}$ electrode pair in step 220.

The software may repeat the prediction subprocess 201 for a given amount of time to determine the window of time at which a given T-index $T_{i,j}{}^t$ remains below the T-index threshold. Iterating the prediction subprocess 201 for a window of time may prevent the brain pacemaker device 100 from responding to false alarms, such as outlier data, which may inadvertently yield an anomalous T-index $T_{i,j}{}^t$. The length of the window may be a configurable parameter stored in memory 110 and may be refined by storing previous durations of entrainment before seizure and updating the length of the window accordingly.

If the software identifies one or more T-indices $T_{i,j}{}^t$ that remain below the T-index threshold for the prescribed window of time, the software retrieves data values for the nonlinear filters F and G and gain factor K corresponding to the identified $i^{th}$ and $j^{th}$ electrodes. The software uses these values, along with the most recently acquired EEG samples (in continuously running step 205) corresponding to the $i^{th}$ and $j^{th}$ electrodes, to implement disentrainment control in step 250.

In step 250, the software implements disentrainment control by computing the external feedback signal $u_{i,j}{}^E$ to negate entrainment as described above. The software executes instructions to compute the feedback signals to be transmitted to the $i^{th}$ and $j^{th}$ transmit electrodes according to the following relation, which was described earlier:

$$u_{i,j}{}^E = G_i^{-1}[-k_{i,j}\{F_j^{-1}[x_j], F_i^{-1}[x_i]\}]$$

$$u_{j,i}{}^E = G_j^{-1}[-k_{j,i}\{F_i^{-1}[x_i], F_j^{-1}[x_j]\}]$$

where $u_{i,j}{}^E$ is transmitted to the $i^{th}$ electrode, and $u_{j,i}{}^E$ is transmitted to the $j^{th}$ electrode. In step 250, the software computes and stores the values for external feedback signals $u_{i,j}{}^E$ and $u_{j,i}{}^E$.

In an exemplary process, the software does this by first computing the gain factor $k_{i,j}=PI\{corr[x_i,x_j]-c^*\}$, which was described earlier, wherein the matrix of T-indices $T_{i,j}{}^t$ was computed in step 210, and the threshold $c^*$ is a configuration parameter that is stored in memory. The software uses the correlation and the threshold $c^*$ as input to a PI control filter to compute $k_{i,j}$ and $k_{j,i}$.

Next, the software retrieves data values corresponding to the parameters for $F^{-1}$ filter 50 and the $G^{-1}$ filter 55, and computes the external feedback signals $u_{i,j}{}^E$ and $u_{j,i}{}^E$ according to the relation above. The $F^{-1}$ filter 50, the $G^{-1}$ filter 55, and the external feedback signals $u_{i,j}{}^E$ and $u_{j,i}{}^E$ may each be in matrix form. Then, the software computes a vector of external feedback signals $u_i{}^E$ according to the following relation:

$$u_i^E = \sum_{\substack{i \neq j}}^{N} u_{i,j}^E.$$

The software may compute the external feedback signals $u_i{}^E$ for all N of the electrodes, or just the critical electrodes identified as showing entrainment in step 220.

In step 255, the software sends the data values for the vector of external feedback signals $u_i{}^E$ to the respective D/A converters 125 via the I/O port 115, which are then converted to analog signals and applied to the corresponding transmit electrodes 135 within the brain sites undergoing entrainment. In accordance with the control paradigm described above, the external feedback signals $u_i{}^E$, injected into the relevant brain sites, breaks the coupling between the corresponding conjectural oscillators and thereby restores spatiotemporal chaos between the critical brain sites.

Process 200 iterates so that if the applied external feedback signals $u_i{}^E$ succeed in disentraining the relevant brain sites, subsequent computation of the T-index $T_{i,j}{}^t$ (in step 210) for the relevant brain sites will return to a value above the T-index threshold. If not, process 200 will continue to iteratively apply newly-computed external feedback signals $u_i{}^E$, computed in step 250, and transmit the signals into the corresponding brain sites until the T-index $T_{i,j}{}^t$ crosses above the T-index threshold. Accordingly, by applying external feedback signals $u_i{}^E$ according to the present invention, seizure may be prevented by eliminating the conditions in which it occurs.

Variations of the brain pacemaker device 100 and process 200 are possible and within the scope of the invention. For example, sensor electrodes 130a-130n and the corresponding transmit electrodes 135a-135n may be integrated into a single set of N electrodes. In other words, a single set of N electrodes may serve as both transmit and sensor electrodes. In this case, in the system identification subprocess 202, adjacent electrodes i and j may respectively serve as transmit electrodes for each other, and the nonlinear filters F and G may be derived based on test signal propagation between adjacent electrodes i and j. It will be readily apparent to one of ordinary skill how the brain pacemaker device 100 may be reconfigured to operate in this manner, or any variation thereof. A further variation may include setting the threshold parameter ca to zero and thus substantially implementing a continuous stimulation/control scheme.

Figure 6A:
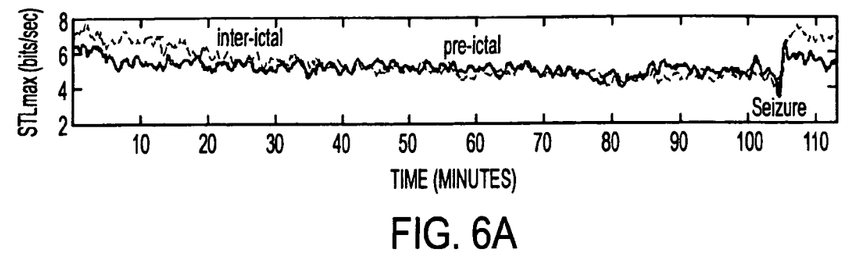
FIGS. 6A-C illustrate exemplary data plots of $STL_{max}$ values, corresponding T-indices, and smoothed cross-correlation coefficients indicating entrainment.

Other methods of computing correlation are possible and within the scope of the invention. FIGS. 6A-C and 7A-C illustrate exemplary data plots of $STL_{max}$, T-index, and smoothed correlation coefficients for different instances of interictal, preictal, and ictal states. FIGS. 6A and 7A illustrate data plots for $STL_{max}$ computed for two electrodes undergoing entrainment over the course of over 100 minutes. Note that the $STL_{max}$ values reach a minimum at the onset of seizure, which is consistent with the loss of spatiotemporal chaos that the critical sites. The seizures identified in FIGS. 6A and 7A return the $STL_{max}$ to their preictal states.

Figure 6B:
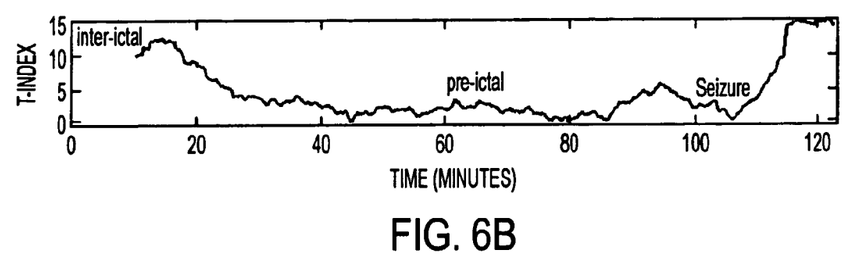
Figure 7A:
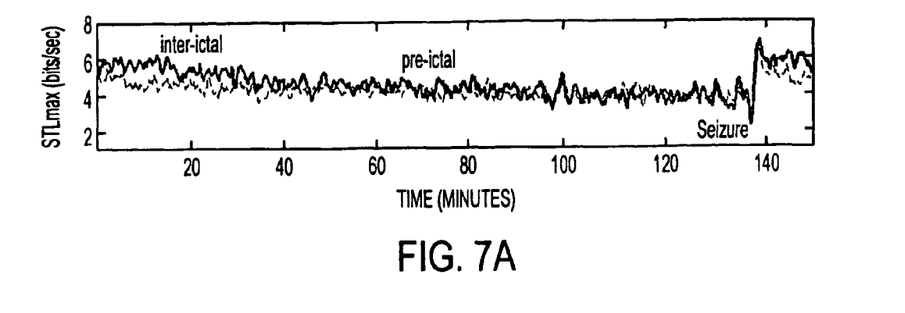
FIGS. 7A-C also illustrate exemplary data plots of $STL_{max}$ values, corresponding T-indices, and smoothed cross-correlation coefficients indicating entrainment.
Figure 7B:
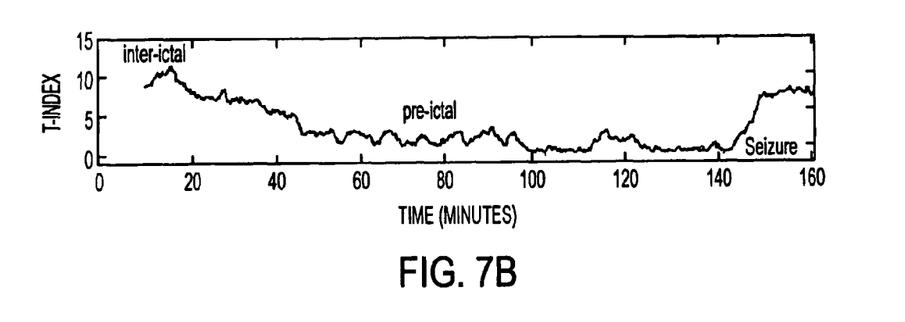

FIGS. 6B. and 7B illustrate exemplary T-index plots corresponding to a pair of critical sites in interictal, preictal, and ictal states. As illustrated in FIGS. 6B and 7B, the T-index plots denote entrainment for up to 60 minutes before seizure.

Figure 6C:
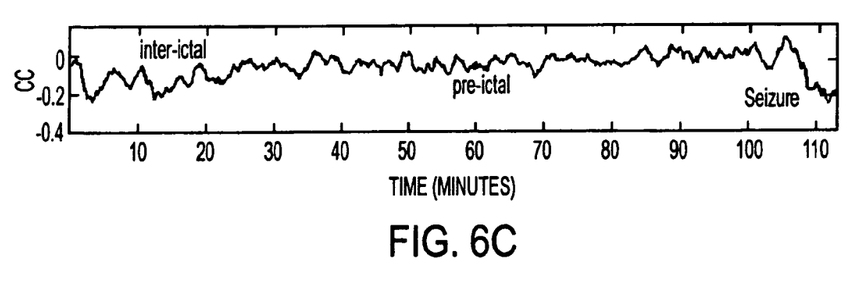
Figure 7C:
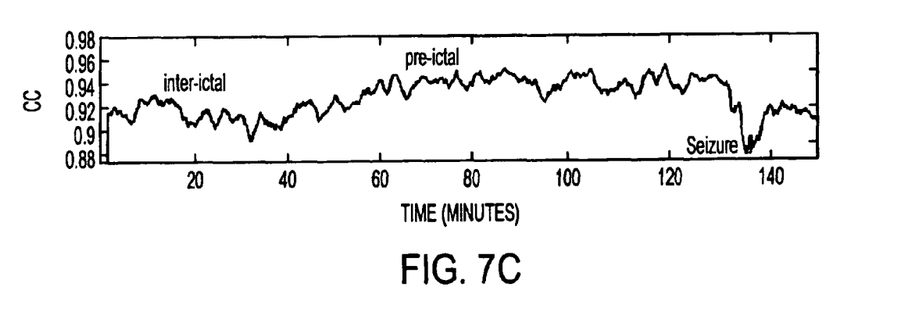

FIGS. 6C and 7C illustrate plots of smoothed cross-correlation coefficients corresponding to a pair of critical sites leading up to seizure. These plots show an upward trend in correlation, signifying a progressive increase in entrainment between the two brain sites. Note that with the onset of seizure, the cross-correlation coefficient values drop. to their interictal state. Accordingly, there are multiple ways of identifying entrainment, in addition to T-index, by which the present invention may predict seizure onset and apply feedback stimuli to prevent it.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for treating a dynamical disorder, comprising:
acquiring a plurality of signals corresponding to a plurality of electrodes, wherein the plurality of electrodes corresponds to a plurality of brain sites;
computing a correlation between a number of signals within the plurality of signals, the number of signals corresponding to a number of brain sites within the plurality of brain sites, wherein computing the correlation comprises computing a T-index value;
computing a feedback signal that is a function of the correlation and the number of signals; and
applying the feedback signal to a number of transmit electrodes within the plurality of electrodes, the number of transmit electrodes corresponding to the number of brain sites.

2. The method of claim 1, wherein the dynamical disorder includes one of epilepsy, Parkinson's Disease, migraines and schizophrenia.

3. The method of claim 1, further comprising:
assembling a state vector corresponding to each electrode within the plurality of electrodes; and
computing a Short Term Lyapunov exponent corresponding to each state vector, before computing the T-index.

4. The method of claim 3, further comprising:
computing an average difference between Short Term Lyapunov exponents, after computing the Short Term Lyapunov exponent; and
computing a standard deviation of differences between Short Term Lyapunov exponents, before computing the T-index.

5. The method of claim 1, wherein computing the feedback signal includes:
deriving a plurality of control parameters;
computing a gain factor based on the correlation and the plurality of control parameters; and
computing the feedback signal based on the plurality of signals and the gain factor.

6. The method of claim 5, wherein computing the gain factor includes applying the correlation, the control parameters, and a threshold to a Proportional Integral feedback mechanism.

7. The method of claim 5, wherein computing the gain factor includes applying the correlation and a threshold to an adaptive feedback mechanism.

8. The method of claim 6, wherein deriving the plurality of control parameters comprises performing a preliminary system identification test.

9. The method of claim 8, wherein performing the preliminary system identification test comprises:
transmitting a plurality of system identification signals to the plurality of electrodes;
acquiring a second plurality of signals corresponding to the plurality of system identification signals; and
determining a plurality of control parameters corresponding to the second plurality of signals and the plurality of system identification signals.

10. The method of claim 1, wherein computing the feedback signal comprises computing a feedback signal that is a function of a threshold.

11. The method of claim 1, wherein computing the feedback signal comprises applying the plurality of signals to a nonlinear filter.

12. The method of claim 1, wherein the plurality of electrodes includes a plurality of sensor electrodes and a plurality of transmit electrodes, wherein each brain site within the plurality of brain sites has a corresponding sensor electrode and transmit electrode.

13. The method of claim 1, further defined as comprising identifying entrainment between the number of brain sites.

14. A device for treating a dynamical disorder, comprising:
a plurality of electrodes corresponding to a plurality of brain sites; and
a microprocessor having a computer readable medium encoded with a program for acquiring a plurality of signals corresponding to the plurality of electrodes; computing a correlation between a number of signals within the plurality of signals, the number of signals corresponding to a number of brain sites within the plurality of brain sites, wherein the program for computing the correlation computes a T-index value; computing a feedback signal that is a function of the correlation and the number of signals; and applying the feedback signal to a number of transmit electrodes within the plurality of electrodes, the number of transmit electrodes corresponding to the number of brain sites.

15. The device of claim 14, wherein the dynamical disorder includes one of epilepsy, Parkinson's Disease, migraines and schizophrenia.

16. The device of claim 14, wherein the program further comprises:
a program for assembling a state vector corresponding to each electrode within the plurality of electrodes; and
a program for computing a Short Term Lyapunov exponent corresponding to each state vector, before computing the T-index.

17. The device of claim 16, wherein the program further comprising comprises:
a program for computing an average difference between Short Term Lyapunov exponents, after computing the Short Term Lyapunov exponent; and
a program for computing a standard deviation of differences between Short Term Lyapunov exponents, before computing the T-index.

18. The device of claim 14, wherein the program for computing the feedback signal comprises:
a program for deriving a plurality of control parameters;
a program for computing a gain factor based on the correlation and the plurality of control parameters; and
a program for computing the feedback signal based on the plurality of signals and the gain factor.

19. The device of claim 18, wherein the program for computing the gain factor includes a program for applying the correlation, the control parameters, and a threshold to a Proportional Integral feedback mechanism.

20. The device of claim 18, wherein the program for computing the gain factor includes a program for applying the correlation and a threshold to an adaptive feedback mechanism.

21. A method for treating a dynamical disorder, comprising:
acquiring a plurality of signals corresponding to a plurality of electrodes, the plurality of electrodes corresponding to a plurality of brain sites identifying entrainment between a number of brain sites within the plurality of brain sites, wherein identifying entrainment comprises computing a T-index and determining if the T-index is below a threshold; and
performing neurocontrol on the number of brain sites, based on a result of identifying entrainment.

22. The method of claim 21, wherein identifying entrainment further comprises determining if the T-index is below a threshold for a window of time.

23. The method of claim 21, wherein performing neurocontrol comprises performing neuromodulation.

24. The method of claim 23, wherein performing neuromodulation comprises:

determining a plurality of control parameters;

determining a correlation between a number of signals corresponding to the number of brain sites;

computing a feedback signal based on the plurality of control parameters and the correlation; and applying the feedback signal to a number of electrodes corresponding to the number of brain sites.

25. The method of claim 21, wherein the dynamical disorder includes one of epilepsy, Parkinson's Disease, migraines and schizophrenia.

26. The method of claim 21, wherein performing neurocontrol comprises minimizing a correlation between a number of signals corresponding to the number of brain sites.

* * * * *

UNITED STATES PATENT AND TRADEMARK OFFICE
CERTIFICATE OF CORRECTION

PATENT NO. : 8,197,395 B2
APPLICATION NO. : 11/632456
DATED : June 12, 2012
INVENTOR(S) : Leonidas D. Jassemidis et al.

It is certified that error appears in the above-identified patent and that said Letters Patent is hereby corrected as shown below:

In claim 17, column 16, line 35, delete "comprising".

Signed and Sealed this
Thirty-first Day of July, 2012

David J. Kappos
*Director of the United States Patent and Trademark Office*